United States Patent
Hunter

(10) Patent No.: US 11,160,819 B2
(45) Date of Patent: Nov. 2, 2021

(54) COMPOSITIONS AND METHODS FOR BOROCARBOHYDRATE COMPLEXES

(71) Applicant: VDF Futureceuticals, Inc., Momence, IL (US)

(72) Inventor: John M. Hunter, South Holland, IL (US)

(73) Assignee: VDF Futureceuticals, Inc., Momence, IL (US)

( * ) Notice: Subject to any disclaimer, the term of this patent is extended or adjusted under 35 U.S.C. 154(b) by 77 days.

(21) Appl. No.: 15/945,654

(22) Filed: Apr. 4, 2018

(65) Prior Publication Data

US 2018/0221398 A1 Aug. 9, 2018

Related U.S. Application Data

(60) Division of application No. 15/213,211, filed on Jul. 18, 2016, now Pat. No. 9,962,399, which is a continuation of application No. 14/791,001, filed on Jul. 2, 2015, now Pat. No. 9,421,216, which is a continuation of application No. 14/473,870, filed on Aug. 29, 2014, now Pat. No. 9,102,700.

(51) Int. Cl.

| | |
|---|---|
| *C07H 23/00* | (2006.01) |
| *A61K 31/7028* | (2006.01) |
| *A61K 31/7024* | (2006.01) |
| *A61K 47/02* | (2006.01) |
| *A61K 9/08* | (2006.01) |
| *C07H 1/00* | (2006.01) |
| *A23L 33/10* | (2016.01) |
| *A23L 2/52* | (2006.01) |

(52) U.S. Cl.
CPC ............ *A61K 31/7028* (2013.01); *A23L 2/52* (2013.01); *A23L 33/10* (2016.08); *A61K 9/08* (2013.01); *A61K 31/7024* (2013.01); *A61K 47/02* (2013.01); *C07H 1/00* (2013.01); *C07H 23/00* (2013.01); *A23V 2002/00* (2013.01)

(58) Field of Classification Search
None
See application file for complete search history.

(56) References Cited

U.S. PATENT DOCUMENTS

| | | | |
|---|---|---|---|
| 5,962,049 | A | 10/1999 | Miljkovic |
| 5,985,842 | A | 11/1999 | Miljkovic |
| 6,080,425 | A | 6/2000 | Miljkovic et al. |
| 6,696,419 | B1 | 2/2004 | Miljkovic |
| 6,924,269 | B2 | 8/2005 | Miljkovic et al. |
| 2005/0032743 | A1 | 2/2005 | Miljkovic |
| 2010/0256076 | A1 | 10/2010 | Pietrzkowski |
| 2013/0287898 | A1 | 10/2013 | Poddar et al. |

FOREIGN PATENT DOCUMENTS

| | | |
|---|---|---|
| GB | 2016446 A | 9/1979 |
| JP | s55145692 A | 11/1980 |
| JP | 2001518882 A | 10/2001 |
| JP | 2003514023 A | 4/2003 |
| RO | 120686 B1 | 6/2006 |
| RO | 121472 B1 | 6/2007 |
| WO | 9843652 | 10/1998 |
| WO | 0135966 A1 | 5/2001 |
| WO | 2012-162108 A2 | 11/2012 |

OTHER PUBLICATIONS

Hansen et al., Synergy of boric acid and added salts in the catalytic dehydration of hexoses to 5-hydroxymethylfurfural in water, www.rsc.org/greenchem, The Royal Society of Chemistry 2011, Green Chem., 2011, 13, pp. 109-114.

Makkee, M., et al., "Studies on borate esters III*. Borate esters of D-mannitol, D-glucitol, D-fructose and D-glucose in water," Laboratory of Organic Chemistry, Delft University of Technology, The Netherlands, Recl. Trav. Chim. Pays-Bas, 104, 230-235 (1985).

Van Duin, M., et al., "Studies On Borate Esters I, The pH Dependence Of The Stability Of Esters Of Boric Acid And Borate In Aqueous Medium As Studied By B. NMR," Tetrahedron, vol. 40, No. 15, pp. 2901-2911 (1984).

Van Duin, M., et al., "Studies On Borate Esters I, The pH Dependence Of The Stability Of Esters Of Boric Acid And Borate In Aqueous Medium As Studied By B. NMR," Tetrahedron, vol. 41, No. 16, pp. 3411-3421 (1985).

Yoshimura, K., et al., "B NMR Studies On Complexation Of Borate With Linear And Crosslinked Polysaccharides," J. Chem. Soc. Faraday Trans., vol. 92, pp. 651-656 (1996).

Untea,A., et al., "Effect Of The Dietary Calcium Fructoborate Given To Weaned Piglets On Calcium Balance," Archiva Zootechnica 11:3, 61-68 (2008).

Scorei, R., et al., "A Double-Blind, Placebo-Controlled Pilot Study To Evaluate The Effect Of Calcium Fructoborate On Systemic Inflammation And Dyslipidemia Markers For Middle-Aged People With Primary Osteoarthritis," Biol. Trace Elem. Res., 144: 253-263 (2011).

Edwards, J.C., et al., "Multinuclear NMR Of Calcium Fructoborate Complex—Structure, Stability, and Quantitation in the Presence Of Other Ingredients, Excipients or Adulterants," Journal of Food Research, vol. 3, No. 3, pp. 115-131 (2014).

(Continued)

*Primary Examiner* — Patrick T Lewis
(74) *Attorney, Agent, or Firm* — Martin Fessenmaier; Umberg Zipser LLP

(57) ABSTRACT

Borocarbohydrate complex containing compositions are presented that have an improved di-complex to boric acid ratio. In some embodiments, compositions are characterized by a di-complex to boric acid ratio of at least 5:1 and more typically at least 10:1 in liquid form, and at least 20:1 in dried form. In other embodiments, compositions are characterized by a minimum content of 80 wt % di-complex and a boric acid content of less than 15 wt %, and more typically less than 5 wt %. Contemplated compositions are thought to have improved biological activity and reduced content of undesired components.

18 Claims, 10 Drawing Sheets

(56) References Cited

OTHER PUBLICATIONS

Militaru, C. et al., "Oral resveratrol and calcium fructoborate supplementation in subjects with stable angina pectoris: Effects on lipid profiles, inflammation markers and quality of life," Nutrition 29, pp. 178-183 (2013).
Rotaru, P., et al., Thermal analysis of a calcium fructoborate sample, Thermochimica Acta, 506, pp. 8-13 (2010).

COMPOSITIONS AND METHODS FOR BOROCARBOHYDRATE COMPLEXES

This application claims priority to and is a divisional application of U.S. patent application Ser. No. 15/213,211, filed Jul. 18, 2016, which is a continuation of U.S. Pat. No. 14,791,001, filed Jul. 2, 2015 and issued on Aug. 23, 2016 as U.S. Pat. No. 9,421,216, which is a continuation of U.S. patent application Ser. No. 14/473,870, filed Aug. 29, 2014 and issued on Aug. 11, 2015 as U.S. Pat. No. 9,102,700. These applications and all other extrinsic materials discussed herein are incorporated by reference in their entirety.

FIELD OF THE INVENTION

The field of the invention is borocarbohydrate complexes, and especially compositions and methods for production of such complexes with improved parameters.

BACKGROUND OF THE INVENTION

The background description includes information that may be useful in understanding the present invention. It is not an admission that any of the information provided herein is prior art or relevant to the presently claimed invention, or that any publication specifically or implicitly referenced is prior art.

For many years, calcium fructoborate (CF) has been a nutritional supplement of interest with many potential medicinal and therapeutic applications. For example, CF has been shown to be an effective antioxidant (Scorei et. al., *Biological Trace Element Research* 107, no. 2 (2005): 127-34), to be effective against cancer (Scorei and Popa, 2010, *Anti-Cancer Agents in Medicinal Chemistry* 10, no. 4 (May 1, 2010): 346-51), and to be a relatively effective modality for reducing inflammation associated with arthritis (Scorei et. al., *Biological Trace Element Research* 144, no. 1-3 (December 2011): 253-63). CF has also been reported for use in the treatment of skin (U.S. Pat. No. 6,080,425) and in attempts to reduce the rate of hair growth (U.S. Pat. No. 5,985,842).

All publications identified herein are incorporated by reference to the same extent as if each individual publication or patent application were specifically and individually indicated to be incorporated by reference. Where a definition or use of a term in an incorporated reference is inconsistent or contrary to the definition of that term provided herein, the definition of that term provided herein applies and the definition of that term in the reference does not apply.

Synthesis of CF has been described in various sources, and one exemplary protocol can be found in U.S. Pat. No. 6,924,269 in which 0.62 g boric acid was reacted with 3.60 g fructose in 10 ml of water, with subsequent neutralization using 1 g calcium carbonate under evolution of carbon dioxide. While such process is at least conceptually simple on paper, it should be recognized that there is substantial complexity involved upon closer investigation. At the outset, commercially available fructose exists in numerous isomeric forms, having five-membered heterocyclic rings (furanose) and six-membered (pyranose) heterocyclic rings, each with their own respective stereoisomeric configuration at the anomeric carbon atom, leading to respective alpha and beta forms. Still further, fructose may also exist in open-chain forms. To complicate matters, the boric acid molecule forms diester complex bonds with two hydroxyl groups of a sugar molecule. As fructose has five hydroxyl groups (several of them in vicinal position), numerous ester products can be formed with each of the stereoisomeric form of fructose. In addition, due to the remaining hydroxyl groups in the boric acid after esterification with a first sugar molecule, further diester complex bonds can be formed with a second sugar molecule, at various positions. Exemplary stereoisomers for fructose are shown in Panel A of FIG. 1, while exemplary mono-complexes are depicted in Panel B of Figure land exemplary di-complexes are depicted in Panel C of FIG. 1. Thus, and not surprisingly, only very little information on reaction dynamics and specific product formation is known for boro-carbohydrate complexes.

For example, Edwards et al. (*Journal of Food Research* 3, no. 3 (May 15, 2014)) report an NMR analysis of fructoborate complexes and their distribution of stereoisomers along with stability data, and Makkee et. al. (*Recueil Des Travaux Chimiques Des Pays-Bas* 104, no. 9 (Sep. 2, 2010): 230-35) describe selected processes for preparation of borate complexes with saccharides in small scale under selected reaction conditions in an attempt to characterize formation of various forms. However, all or almost all of the conditions that were described as providing CF as a di-complex suffered from very low yields and/or substantial residual quantities of boric acid, which is generally undesirable. For example, Makkee et al. showed that the di-complex can be favored in reactions at high pH that utilize a large (5:1 or 10:1) fructose to boron molar ratio, however the overall yield of the CF di-complex is very poor, leaving excess quantities of free fructose which leads to a significant dilution of the desired product. On the other hand, where the fructose to boron molar ratio was reduced, free boric acid content almost exponentially increased at concurrent loss of di-complex versus mono-complex. Residual boric acid is also very undesirable due to its potential toxicity and other possible interference with biological molecules (e.g., boric acids are known to act as inhibitor to certain enzymes (e.g., urease) or Rho family of GTP-binding proteins). Such lack of specific guidance is especially disappointing as it has been speculated that the di-complex is the biologically most relevant and therefore most desirable form of CF.

Thus, while CF and other carbohydrate complexes are well known in the art, there is still a need for a process that results in a high-yield of di-complex calcium fructoborate or other boro-carbohydrate complexes. Viewed from a different perspective, it would be desirable to have a process that provides a composition comprising calcium fructoborate or other boro-carbohydrate complex with low (e.g., ≤10 wt %) residual free boric acid in the product. In the same way, it would be desirable to have a process that provides a composition with calcium fructoborate or another boro-carbohydrate complex without large amounts (e.g., ≥30 wt %) of residual fructose or other carbohydrate in the product. Finally, and viewed from yet another perspective, it would be desirable to have a process that provides a composition with a di-complex to free boric acid ratio that is at least 10:1, more preferably at least 15:1, and most preferably at least 20:1.

SUMMARY OF THE INVENTION

The inventive subject matter is directed to various borocarbohydrate complex-containing compositions and methods of their production. In especially noteworthy aspects of the inventive subject matter, the borocarbohydrate complex-containing compositions have a very high content of di-complex, a very low content of unreacted boric acid, and are obtained at remarkably high yields.

In one aspect of the inventive subject matter, The inventors contemplate a method of producing a composition that comprises borocarbohydrate complexes in an amount of at least 65 wt %, wherein the borocarbohydrate complexes include di-complexes and mono-complexes, wherein the composition further comprises boric acid, and wherein the di-complex and the boric acid are present in a ratio of at least 10:1. Particularly contemplated methods include a step of selecting a molar ratio between a carbohydrate and the boric acid of at least 1.8:1, and a further step of selecting a preparative scale for the reaction of at least 1000 ml. The carbohydrate is then reacted with the boric acid at the ratio and the scale to thereby form the carbohydrate complexes. In most embodiments, a cation is added to form a salt of the carbohydrate complexes.

In some aspects, the step of reacting forms the carbohydrate complexes in an amount of 70 wt %, and/or the molar ratio between the carbohydrate and the boric acid is between 1.8:1 and 2.4:1, and/or the preparative scale for the reaction is at least 5,000 ml. Therefore, it is also contemplated that the di-complex and the boric acid are present in a ratio of at least 15:1, or in a ratio of at least 20:1. Most typically, the composition is a liquid composition, and/or the carbohydrate is fructose, and/or the cation is a calcium cation or a magnesium cation. It is further contemplated that the composition has a pH of less than 6.0.

Viewed from a different perspective, the inventors also contemplate a method of producing a composition comprising borocarbohydrate complexes having a borocarbohydrate di-complex to boric acid ratio of at least 5:1. In such methods, a molar ratio between the carbohydrate and the boric acid of at least 1.6:1 is selected and a preparative scale for the reaction of at least 200 ml is selected. The carbohydrate is then reacted with the boric acid and a compound that comprises a cation at an acidic pH and at the ratio and the scale to so form the carbohydrate complexes, wherein the carbohydrate complexes form a salt with the cation.

In most aspects, the molar ratio between the carbohydrate and the boric acid is between 1.8:1 and 2.4:1, and/or the preparative scale for the reaction is at least 1,000 ml, and/or the acidic pH is a pH of less than 6.0. Most typically, the borocarbohydrate complexes are present in the composition in an amount of at least 60 wt %, and/or the borocarbohydrate di-complex to boric acid ratio is at least 10:1. The compound that comprises a cation is in many embodiments an alkaline metal hydroxide, an earth alkaline metal hydroxide, an alkaline metal carbonate, or an earth alkaline metal carbonate, and/or the carbohydrate is fructose.

Therefore, the inventors also contemplate a method of increasing di-complex content in a preparative reaction having a first reaction scale to form a composition comprising at least 65 wt % borocarbohydrate complexes, wherein the borocarbohydrate complexes are a mixture of di-complexes and mono-complexes. Such methods will typically include a step of selecting a molar ratio between the carbohydrate and the boric acid of at least 1.4:1, and a further step of increasing the first reaction scale (e.g., at least 200 ml) to a second reaction scale, and reacting the carbohydrate and the boric acid at the ratio at the second reaction scale (e.g., at least 1,000 ml) to thereby increase the di-complex content in the second reaction scale as compared to the first reaction scale.

In preferred embodiments the carbohydrate is fructose, and/or the step of increasing the first reaction scale to the second reaction scale also decreases unreacted boric acid in the second reaction scale as compared to the first reaction scale. In most embodiments, the molar ratio between the carbohydrate and the boric acid is between 1.8:1 and 2.4:1. Where desired, water can be removed from the composition (e.g., via freeze-drying or spray drying).

Thus, viewed from a different perspective, and in a method of producing a composition comprising borocarbohydrate complexes and boric acid, wherein the borocarbohydrate complexes are a mixture of di-complexes and a mono-complexes, an improvement may comprise a step of reacting a carbohydrate with boric acid at an acidic pH and at a molar ratio between the carbohydrate and the boric acid of at least 1.8:1, wherein the step of reacting is performed at a preparative scale of at least 1000 ml to thereby achieve a ratio of di-complex to residual boric acid of at least 10:1.

Most typically, the carbohydrate is fructose, and/or the pH is less than 6.0, and/or the molar ratio between the carbohydrate and the boric acid is between 1.8:1 and 2.4:1. Therefore, the ratio of di-complex to residual boric acid of at least 15:1 or at least 20:1. As before, it is contemplated that such improvements may include a step of removing water from the composition.

In yet another aspect of the inventive subject matter, a method of producing a composition with a boric acid content of equal or less than 15 wt % is contemplated, wherein the composition comprises at least 70 wt % borocarbohydrate complexes, and wherein the borocarbohydrate complexes are a mixture of di-complexes and mono-complexes. Such methods will include a step of selecting a molar ratio between the carbohydrate and the boric acid such that the carbohydrate is in molar excess over the boric acid, and a further step of selecting a preparative scale for the reaction of at least 1000 ml, and a still further step of reacting the carbohydrate and the boric acid at an acidic pH to thereby produce the composition with the boric acid content of equal or less than 15 wt %.

In such methods, it is contemplated that the boric acid content of the composition is equal or less than 10 wt % or equal or less than 5 wt %, and/or that the molar ratio between the carbohydrate and the boric acid is between 1.6:1 and 2.2:1, and/or that the acidic pH is a pH of less than 6.0.

Consequently, the inventors also contemplate a liquid composition that comprises a plurality of borocarbohydrate complexes and boric acid, wherein the borocarbohydrate complexes are a mixture of a di-complex and a mono-complex, and wherein the di-complex is present in the composition in an amount of at least 75 wt % and wherein the boric acid constitutes less than 13 wt % of the composition.

Most typically, the ratio of the di-complex to the mono-complex in the mixture is between 10:1 and 12:1, and/or the di-complex is present in the composition in an amount of at least 80 wt % or at least 85 wt %, while unreacted boric acid is present in the composition in an amount of less than 10 wt %, or less than 5.0 wt %.

Viewed from a different perspective, the inventors also contemplate a liquid composition having an acidic pH and comprising a borocarbohydrate di-complex and boric acid, wherein the borocarbohydrate di-complex and the boric acid are present in a ratio of at least 10:1. The acidic pH in such compositions is a pH of less than 6.0, and/or the borocarbohydrate di-complex and the boric acid are present in a ratio of at least 15:1, or at least 20:1, while the unreacted boric acid is present in an amount of less than 10 wt % or less than 5 wt %. It is further contemplated that in such compositions the borocarbohydrate di-complex is present in an amount of at least 80 wt %.

In yet another aspect of the inventive subject matter, the inventors also contemplate a liquid composition comprising a borocarbohydrate di-complex, a borocarbohydrate mono-complex and boric acid, wherein a ratio between the borocarbohydrate di-complex and the borocarbohydrate mono-complex is at least 10:1, and wherein the boric acid is present in the composition in an amount of equal or less than 10 wt %.

The ratio between the borocarbohydrate di-complex and the borocarbohydrate mono-complex in such compositions is at least 15:1, or at least 20:1, and/or the ratio between the borocarbohydrate di-complex and the borocarbohydrate mono-complex is at least 25:1, while in further aspects the boric acid is present in the composition in an amount of equal or less than 7.5 wt %, or less than 5.0 wt %. Most typically, the liquid composition has a pH of less than 6.0.

Therefore, the inventors also contemplate a liquid reaction mixture having an acidic pH comprising a carbohydrate, boric acid, and borocarbohydrate complexes, wherein the borocarbohydrate complexes are a mixture of di-complexes and mono-complexes, and wherein the di-complexes and the boric acid are present in a ratio of at least 5:1, and wherein a ratio of the borocarbohydrate complexes to the carbohydrate is between 1.5 and 4.5. Most typically, the ratio of the borocarbohydrate complexes to the carbohydrate is between 2.0 and 3.5, and/or the pH is less than 6.0 while the liquid reaction mixture has a volume of at least 200 ml.

Moreover, the inventors also contemplate a composition comprising a borocarbohydrate di-complex and unreacted boric acid, wherein the borocarbohydrate di-complex and the boric acid are present in the composition in a ratio of at least 10:1 in liquid form and at least 20:1 in dried form. In such compositions, the borocarbohydrate di-complex and the boric acid are present in the composition at a ratio of at least 15:1 in liquid form and at least 22:1 in dried form, and/or the boric acid is present in the composition in an amount of less than 10 wt %, or less than 5.0 wt %.

In view of the above, a composition is also contemplated comprising a borocarbohydrate complex that is produced by a process having the steps of (a) selecting a molar ratio between the carbohydrate and the boric acid of at least 1.6:1; (b) selecting a preparative scale for the reaction of at least 1000 ml; and (c) reacting the carbohydrate and the boric acid at an acidic pH to thereby obtain a composition that comprises a borocarbohydrate di-complex and boric acid at a ratio of at least 5:1.

Most typically, the molar ratio between the carbohydrate and the boric acid is between 1.8:1 and 2.2:1, and/or the acidic pH is a pH of less than 6.0, and/or the composition comprises the borocarbohydrate di-complex and the boric acid at a ratio of at least 10:1 or at least 15:1.

Various objects, features, aspects and advantages of the inventive subject matter will become more apparent from the following detailed description of preferred embodiments, along with the accompanying drawing figures in which like numerals represent like components.

BRIEF DESCRIPTION OF THE DRAWING

FIG. 3A lists di-complex ('di-ester') formation as a function of molar ratio; FIG. 3B shows the ratio of di-complex to unreacted boric acid as a function of molar ratio; FIG. 3C provides compositional information about stereochemical aspects in fructoborate complexes as a function of molar ratio; FIG. 3D is a line graph showing corresponding compositional information about stereochemical aspects in unreacted fructose as a function of molar ratio; FIG. 3E illustrates yields of total fructose complexes (mono- and di-complexes) relative to unreacted fructose as a function of molar ratio; FIG. 3F is a line graph illustrating the ratio of total fructose complexes to unreacted fructose as a function of molar ratio.

FIG. 4A illustrates yields of total fructose complexes (mono- and di-complexes) relative to unreacted fructose as a function of molar ratio; FIG. 4B is a line graph illustrating the ratio of total fructose complexes to unreacted fructose as a function of molar ratio.

FIG. 5A is a line graph showing a decrease of free (unreacted) boric acid as a result of scale up at the same molar ratios over a range of preset molar ratios. FIG. 5B is a line graph showing an increase of di-complex as a result of scale up at the same molar ratios over a range of preset molar ratios. FIG. 5C is a line graph showing that the quantities of mono-complex is substantially unaffected by scale up at the same molar ratios over a range of preset molar ratios. FIG. 5D is a bar graph showing an increase of the ratio of di-complex to free boric acid as a result of scale up and an exacerbated increase of the same ratio as a function of molar ratios between fructose and boric acid. FIG. 5E is a bar graph indicating that the ratio of di-complex to mono-ester is substantially unaffected by scale up and molar ratios between fructose and boric acid.

FIG. 6A shows ratios of di-complex to free boric acid in liquid, reconstituted freeze-dried (FD), and reconstituted spray-dried (SD) forms as a function of production scale. FIG. 6B shows ratios of di-complex to free boric acid in various production scales as a function of state (liquid, reconstituted freeze-dried (FD), and reconstituted spray-dried (SD)).

DETAILED DESCRIPTION

Figure 1:
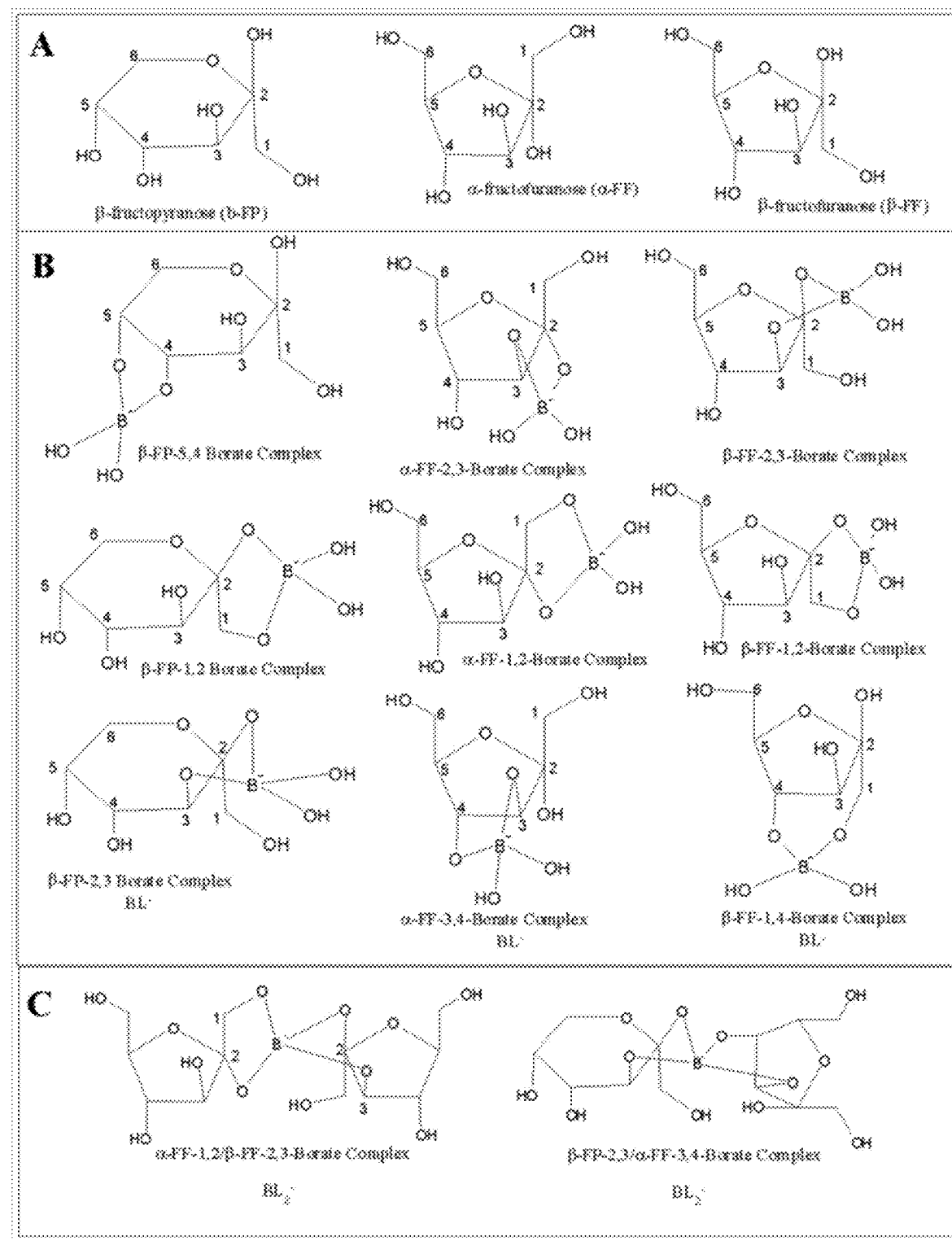
FIG. 1 shows exemplary stereoisomeric forms of fructose (Panel A), fructoborate mono-complexes (Panel B), and fructoborate di-complexes (Panel C).

The inventors have discovered various methods and conditions that allow production of borocarbohydrate complex-containing compositions with high content of di-complexes, very low content of unreacted boric acid, and low quantities of unreacted fructose, all at remarkably high yields.

For example, in some aspects of the inventive subject matter, and as described in more detail below, total carbohydrate complexes could be produced at yields of ≥60 wt %, ≥65 wt %, ≥70 wt %, or ≥75 wt %. In other aspects of the inventive subject matter, and as also described in more detail below, unreacted boric acid was limited to quantities of ≤10 wt %, ≤8 wt %, ≤6 wt %, or ≤4 wt %. In yet further aspects of the inventive subject matter, and as described in more detail below, the yields of the di-ester were remarkably high, for example, at a di-ester to mono-ester ratio of at least 8:1, at least 9:1, at least 10:1, or at least 11:1, and/or at a di-ester to unreacted boric acid of at least 9:1, at least 10:1, at least 15:1, at least 20:1, or at least 25:1 as also shown in more detail below. Therefore, in still other aspects of the inventive subject matter, total carbohydrate complexes can be produced with low residual quantities of carbohydrate, at for example, ≤35 wt %, ≤30 wt %, ≤25 wt %, or ≤20 wt % unreacted carbohydrate. Unless specified otherwise, all percentages are indicated as wt % of the total of all reaction products and unreacted reagents.

Despite the seemingly simple reaction of boric acid and carbohydrates to form esters, the inventors discovered that numerous reaction parameters have unexpected and significant impact on various aspects of product formation, and especially on quantities of di-complex, overall yield of borocarbohydrate complexes, and residual (unreacted) boric acid. For example, while a molar excess of boric acid over fructose generally increases overall complex formation, inverting these molar proportions (e.g., using slight molar excess of fructose over boric acid) lead to an optimum area of di-complex formation with apparent saturation starting at a ratio of about 1.8. Even more unexpectedly, increasing the molar ratio of fructose to boric acid (between 1:1 and 3:1) revealed that at a ratio of about 2.2-2.4:1 free boric acid was at a minimum, but that there was a balance point in maximizing yield of complex formation (where a lower fructose to boric acid ratio was better) and free boric acid (where a higher fructose to boric acid ratio was better). Additionally, the inventors unexpectedly discovered that a simple scale-up of the reaction at particular molar ratios of carbohydrate to boric acid ratio using otherwise identical process conditions decreased unreacted boric acid and also increased the yield of the di-complex (especially at molar ratios of carbohydrate to boric acid ratio of 1.4:1 to 2.2:1). Oddly, the formation of mono-complexes was substantially unaffected.

In another unexpected finding on scale-up, the inventors also discovered that the ratio of di-complex to free boric acid was almost entirely insensitive to scale-up where the molar ratios of fructose to boric acid was below 1.6:1 (e.g., 1.4:1 to 1.6:1), was only slightly affected at a molar ratio of fructose to boric acid of 1.8:1, and was substantially affected (e.g., almost linear at 2.0:1) with an apparent optimum 5L scale for 2.2:1 as also shown in more detail below.

It should be appreciated that while specific examples below are provided with respect to fructose as the carbohydrate, numerous other carbohydrates are also deemed suitable for use herein, and especially nutritionally acceptable carbohydrates. Thus, alternative carbohydrates generally include various hexoses and pentoses, which may be in aldose or ketose form, and which may be (when in ring form) present as furanose or pyranose carbohydrate. Viewed from a different perspective, suitable carbohydrates include various monosaccharides, disaccharides, oligosaccharides, and polysaccharides, all of which may be natural or synthetic. Exemplary carbohydrates therefore include glucose, fructose, galactose, sucrose, maltose, lactose, etc. Moreover, alternative compounds to carbohydrates include various polyols, and especially nutritionally and/or pharmaceutically acceptable polyols, as well as other nutritionally and/or pharmaceutically acceptable compounds with germinal or 1,3-diol groups. While not limiting to the inventive subject matter, it is also contemplated that the carbohydrates may include one or more isotopic atoms (e.g., $^{13}C$, $^{14}C$, $^{2}H$, $^{17}O$ or $^{18}O$). Similarly, it is generally preferred that the boron in the borocarbohydrate complexes is provided in the form of boric acid, and most typically in the form of an aqueous solution. However, in other aspects of the inventive subject matter, boron may be provided as borax solution, or as a boronic acid.

In many embodiments, the preparation of the borocarbohydrate complexes is based on reacting fructose in solution with boric acid for a time sufficient to allow the reaction to run to completion and/or the reaction mixture to become clear (e.g., at least 30 min, at least 60 min, or at least 90 min). After the reaction is completed, the borocarbohydrate complexes can be charge neutralized with a cation-containing compound, which is preferably an alkaline metal hydroxide, an earth alkaline metal hydroxide, an alkaline metal carbonate, and/or an earth alkaline metal carbonate (e.g., calcium carbonate). Most typically, the cation-containing compound is added in an amount that is between an equimolar amount (with respect to boric acid) and 10% of the molar amount of boric acid, most typically between 0.7 and 0.3 (e.g., 0.5) times the molar amount of boric acid. Where the cation-containing compound is a hydroxide or carbonate, it is in most aspects preferred that the cation-containing compound is added slowly (e.g., over a period of at least 10 min, at least 20 min, or at least 30 min), and where appropriate in multiple batches (e.g., at least two, three or four, etc.). The so prepared liquid composition can then be further combined with other components, or compounded with one or more beverages. Alternatively, water can be at least partially removed to obtain a concentrate or dry product (e.g., via freeze drying or spray drying) that can then be used as or compounded with a nutritional supplement.

Experiments and Results

Unless indicated otherwise, all reactions were performed at the indicated scale and molar ratios between fructose and boric acid by first dissolving fructose in water at a temperature of 20-25° C. Solid boric acid is then added at the selected molar ratio, and the mixture is reacted under continuous stirring for 90 minutes at a temperature of 20-25° C. Where desired, $CaCO_3$ is then added in an amount that is 50% of the molarity of the boric acid over a period of 30 minutes in three equal batches under continuous stirring (e.g., where 1 mol of boric acid was used, 0.5 mol $CaCO_3$ was used). The pH of the reaction was typically neutral to moderately acidic, and in most cases at a pH of less than 6.0.

Liquid-state $^{11}B$, $^{13}C$, and $^{1}H$ NMR was performed on a Varian Mercury 300MVX NMR spectrometer equipped with a 5 mm Varian ATB Probe at resonance frequencies of 96.14 MHz ($^{11}B$), 75.36 MHz ($^{13}C$) and 299.67 MHz ($^{1}H$), respectively. $^{11}B$ spectra were acquired with a 45 degree tip angle pulse width, a relaxation delay of 0.2 seconds, an acquisition time of 80 ms with 8K points acquired with a spectral width of 100 kHz, and 1024 pulses were averaged. The data was zero filled to 65K points. The $^{13}C$ NMR was acquired with a 30 degree tip angle pulse width, a relaxation delay of 5 seconds, 0.96 second acquisition time, with 24K points acquired with a spectral width of 25 kHz, and 10-12,000 pulses were averaged. The data was zero filled to 131K points. The $^{1}H$ NMR spectra were obtained with a 30 degree pulse angle, a relaxation delay of 2 seconds, a 4.448 second acquisition time, with 32K points acquired over a spectral width of 7.2 kHz, and 128 pulses were averaged. The data was zero-filled to 131K points. The data was acquired in a quantitative manner with inverse gated decoupling of protons during the acquisition of the $^{11}B$ and $^{13}C$ experiments. All samples were dissolved in $D_2O$ (Cambridge Isotope Laboratories). No pH adjustments were performed on the samples after dissolution.

Solid-State $^{13}C$ (50.30 MHz), $^{11}B$ (64.17 MHz) NMR spectra were obtained on a Varian UnityPlus-200 NMR spectrometer equipped with a Doty Scientific 7 mm Supersonic CP-MAS probe. Magic angle spinning (MAS) speeds of around 6 kHz were employed. The $^{13}C$ NMR data was acquired using cross polarization which prepares the magnetization on the protons initially and then transfers the spin locked magnetization to the $^{13}C$ nuclei. The advantage of this experiment is the fact that it is performed at the spin-lattice relaxation rate (T1) of protons in the sample which is considerably shorter than the T1 of $^{13}C$ nuclei in the same sample. Thus, one obtains a significant enhancement of the $^{13}C$ signal from the polarization transfer and can pulse at a shorter pulse-repetition rate. The $^{13}C$ CP-MAS experiment on calcium fructoborate complex was performed with a 1 ms variable amplitude contact time, an 8 second relaxation rate, and an acquisition time of 25.6 ms, with 1K points being acquired over a spectral with of 40 kHz, and 4096 pulses were averaged. The exceptions to these acquisition parameters were those used for pure crystalline fructose. The $^{11}B$ NMR spectra were acquired with MAS and with the sample remaining static in the NMR probe. The experiments were acquired with a central transition selective pulse width, a 0.2 second relaxation time, with 1K points being acquired in an acquisition time of 10.2 ms, and with a spectral width of 100 kHz.

Samples were observed directly after they were received, after they had been thermally treated in a Duratech TCON dry bath system (capable of holding temperatures to +/−0.1° C.), or as calibration standards which were made by mixing accurately weighed samples of calcium fructoborate with magnesium stearate or maltodextrin. Samples for solid-state NMR were weighed to the nearest 0.1 mg on a Sartorius GD-503-NTEP microbalance after they were packed into the MAS rotor.

Figure 2A:
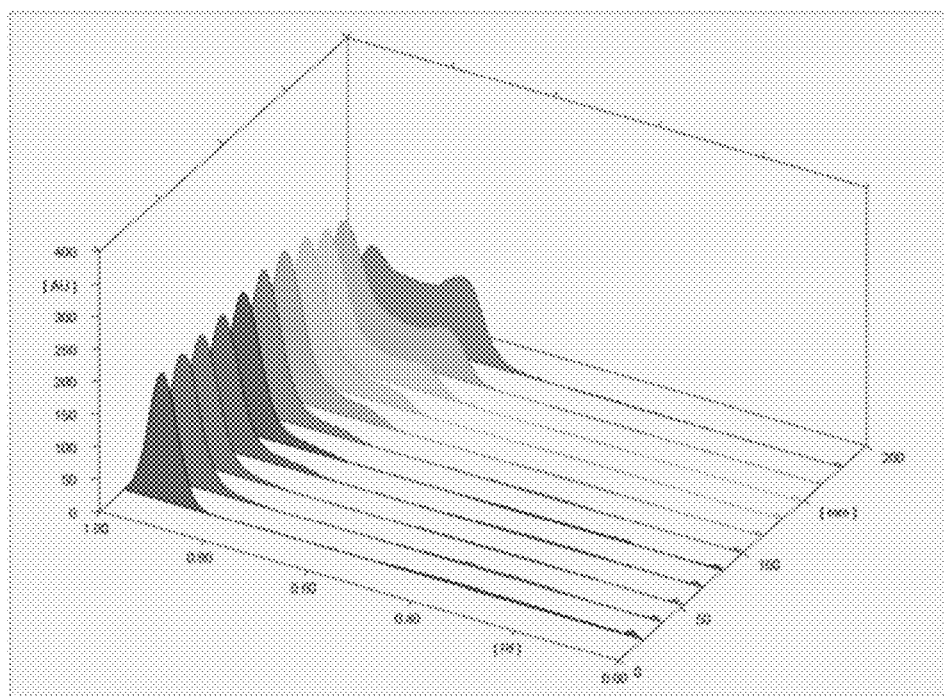
FIGS. 2A and 2B show graphs for densitometry readings of TLC tracks. Tracks in FIG. 2A represent individual reactions of fructose and boric acid with molar ratios ranging from 1:10 to 1:1, and tracks in FIG. 2B represent individual reactions of fructose and boric acid with molar ratios ranging from 1:1 to 10:1.
Figure 2B:
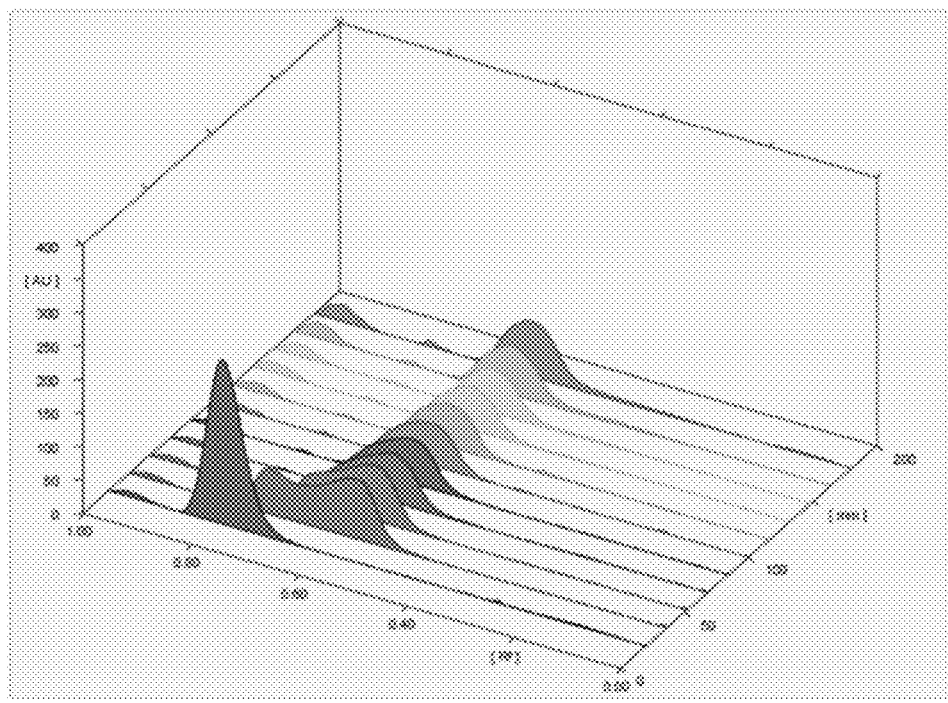

Initial studies had shown that overall borocarbohydrate complex formation was favored under substantial molar excess of boric acid relative to fructose as can be seen from FIGS. 2A and 2B. More particularly, FIG. 2A illustrates optical densitometry readings from a TLC plate onto which were spotted aliquots of small scale reaction volumes (e.g., 2 ml) with decreasing molar ratios between fructose and boric acid. Reading the lanes from front to back, the first lane is fructose control, while the following next 10 lanes reflect a decrease starting at 10:1 (fructose to boric acid) to 1:1 (fructose to boric acid). As is readily evident, appreciable quantities of total complex formation begin to develop at equimolar ratios (see last lane). Similarly, FIG. 2B illustrates optical densitometry readings from a TLC plate onto which were spotted aliquots of small scale reaction volumes (e.g., 2 ml) with increasing molar ratios between boric acid and fructose. Again, reading the lanes from front to back, the first lane is fructose control, while the following next 10 lanes reflect an increase starting at 1:1 (fructose to boric acid) to 1:10 (fructose to boric acid). As can be seen, appreciable total complex formation is favored at a molar ratio of 1:2 (fructose to boric acid), and is nearly quantitative at a molar ration of 1:5 (fructose to boric acid). Thus, under the conditions observed, molar excess of boric acid drove the formation of total borocarbohydrate complex yield.

In an effort to further investigate the reaction conditions and product compositions, the inventors performed numerous experiments at various production scales and various molar ratios between the carbohydrate (e.g., fructose) and boric acid. Quite unexpectedly, the inventors found that the specific product composition is substantially affected by at least the molar ratios between the carbohydrate (e.g., fructose) and boric acid and/or the production scale. Contrary to the skilled artisan's approach of using a high boric acid to carbohydrate ratio to so increase overall yield of the borocarbohydrate complex as suggested by the data in FIGS. 2A and 2B, the inventors discovered that by selection of the appropriate molar ratio between the carbohydrate and the boric acid an enhanced yield of di-complex can be obtained at concurrent low quantities of unreacted boric acid.

For example, the inventors modified the molar ratio between the carbohydrate (here:fructose) and boric acid over a relatively large range from an equimolar ratio to a 3:1 molar excess of fructose to boric acid at a 200 ml production scale. Notably, based on quantitative $^{11}B$ NMR analysis and as can be clearly seen in Table 1 below, quantities of unreacted boric acid significantly decreased with increasing molar ratio (in the range from 1.0:1 to 2.4:1), and then moderately rose with further increasing molar ratio (in the range from 2.6:1 to 3.0:1. Thus, it should be appreciated that an increase in the molar ratio between the carbohydrate (here:fructose) and boric acid over a range of at least 1.8:1 to 2.6:1 had the unexpected technical effect of decreasing quantities of unreacted boric acid. Conversely, the quantities of the di-complex increased as a function of an increasing molar ratio between the carbohydrate (here:fructose) and boric acid over a relatively large range from an equimolar ratio to a 3:1 molar excess of fructose to boric acid at a 200 ml production scale, possibly with a saturation effect starting at a molar ratio of about 1.8:1. Thus, compositions with especially high di-complex content could be obtained at molar ratios at and above 1.6:1 or 1.8:1. Therefore, an increase in the molar ratio between the carbohydrate (here:fructose) and boric acid starting at 1.6:1 or 1.8:1 had the unexpected technical effect of increasing quantities of di-ester. Remarkably, the increase in molar ratio between fructose and boric acid had little to no effect on the quantities of mono-ester produced by the reaction.

Figure 3A:
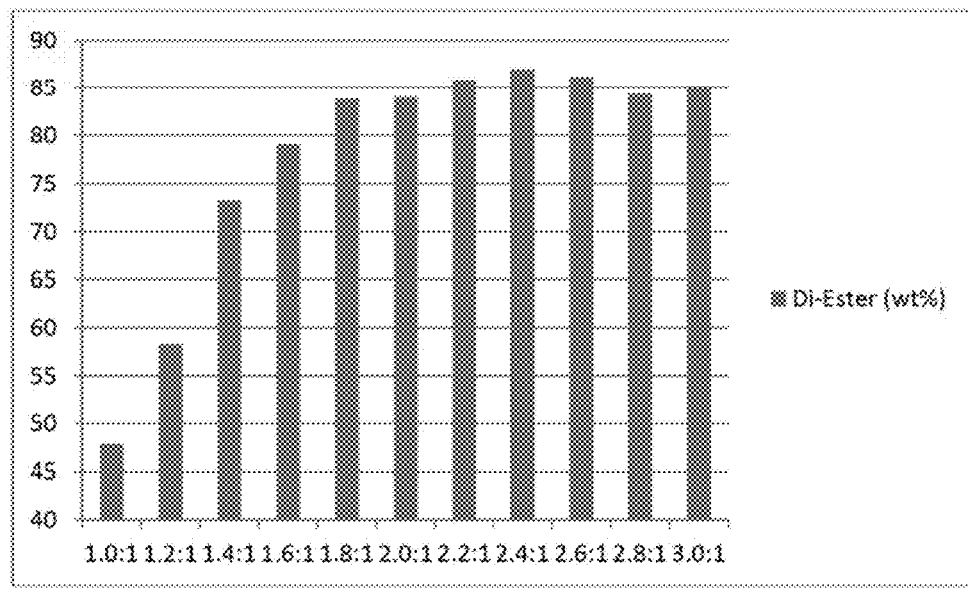
FIGS. 3A to 3F illustrate exemplary results for selected product parameters at a 200 ml scale and molar ratios of fructose to boric acid between 1:1 and 3:1.
Figure 3B:
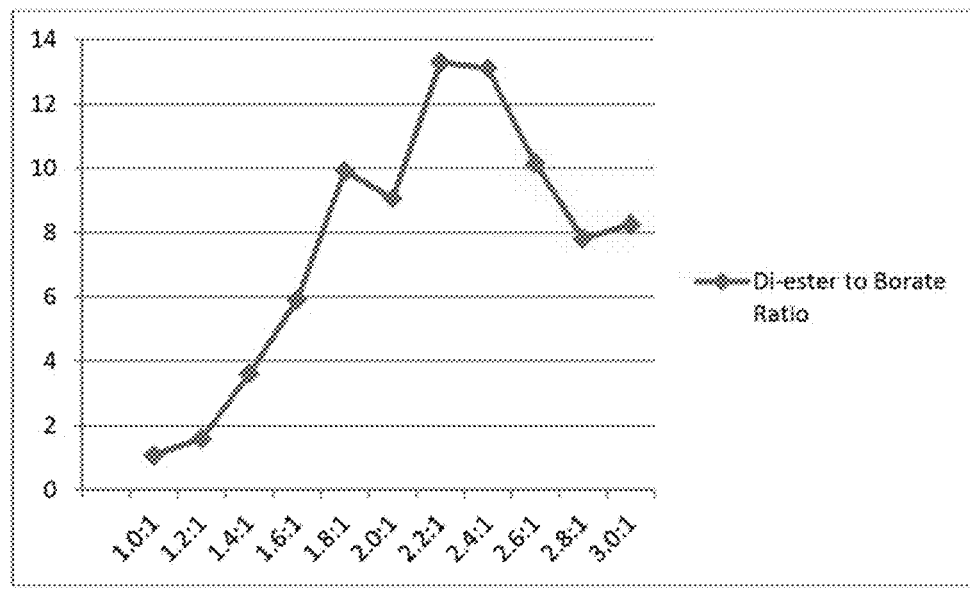

FIG. 3A exemplarily illustrates the dramatic increase in di-ester yield as a function of increasing molar ratio between the carbohydrate (here:fructose) and boric acid. The ratio of di-ester to unreacted boric acid is exemplarily depicted in FIG. 3B, where the optimum range for the ratio is between 1.8:1 and 2.6:1.

TABLE 1

| Molar Ratio | Borate (wt %) | Di-Ester (wt %) | Mono-ester (wt %) | Di-ester/Borate Ratio |
|---|---|---|---|---|
| | | Volume 200 ml | | |
| 1.0:1 | 44.34 | 47.84 | 7.81 | 1.08 |
| 1.2:1 | 36.42 | 58.26 | 5.32 | 1.60 |
| 1.4:1 | 20.32 | 73.28 | 6.40 | 3.61 |
| 1.6:1 | 13.38 | 79.12 | 7.50 | 5.91 |
| 1.8:1 | 8.46 | 83.84 | 7.70 | 9.91 |
| 2.0:1 | 9.28 | 84.04 | 6.68 | 9.05 |
| 2.2:1 | 6.46 | 85.86 | 7.67 | 13.28 |
| 2.4:1 | 6.64 | 87.01 | 6.35 | 13.10 |
| 2.6:1 | 8.50 | 86.19 | 5.31 | 10.14 |
| 2.8:1 | 10.78 | 84.33 | 4.89 | 7.82 |
| 3.0:1 | 10.30 | 85.02 | 4.68 | 8.25 |

Figure 3C:
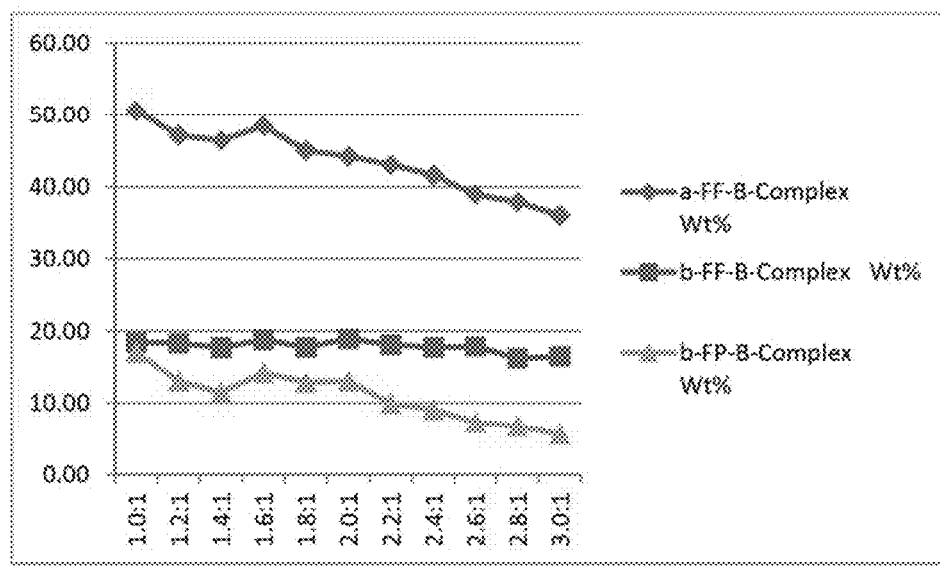

Remarkably, $^{13}C$ NMR analysis also revealed that an increase in the molar ratio of carbohydrate (here:fructose) to boric acid decreased total complex (di-plus mono-complex) formation most significantly for the alpha-fructofuranose form, moderately for the beta-fructofuranose form, and negligibly or not for the beta-fructopyranose form as can be taken from Table 2 below. Also, the most pronounced decrease in total complex forms for the alpha-fructofuranose form and the beta-fructofuranose form started at a ratio of 1.6:1 or 1.8:1, which appears to be a counter-trend to the specific increase in di-ester formation at comparable ratios. Thus, an increase of the molar ratio of carbohydrate (here: fructose) to boric acid above 1.6:1 or 1.8:1 had the surprising technical effect of decreasing total complexes in alpha-fructofuranose form and to some extent beta-fructofuranose form. FIG. 3C is a graphic representation of the results of Table 2.

TABLE 2

| Molar Ratio | a-FF-B-Complex (wt %) | b-FF-B-Complex (wt %) | b-FP-B-Complex (wt %) |
|---|---|---|---|
| | Volume 200 ml | | |
| 1.0:1 | 50.58 | 18.42 | 17.02 |
| 1.2:1 | 47.15 | 18.31 | 13.02 |
| 1.4:1 | 46.44 | 17.68 | 11.47 |
| 1.6:1 | 48.44 | 18.79 | 14.20 |
| 1.8:1 | 45.00 | 17.79 | 12.89 |
| 2.0:1 | 44.19 | 18.93 | 13.02 |
| 2.2:1 | 43.00 | 18.10 | 9.97 |
| 2.4:1 | 41.60 | 17.75 | 9.12 |
| 2.6:1 | 38.97 | 17.88 | 7.34 |
| 2.8:1 | 37.93 | 16.21 | 6.80 |
| 3.0:1 | 36.05 | 16.49 | 5.70 |

Figure 3D:
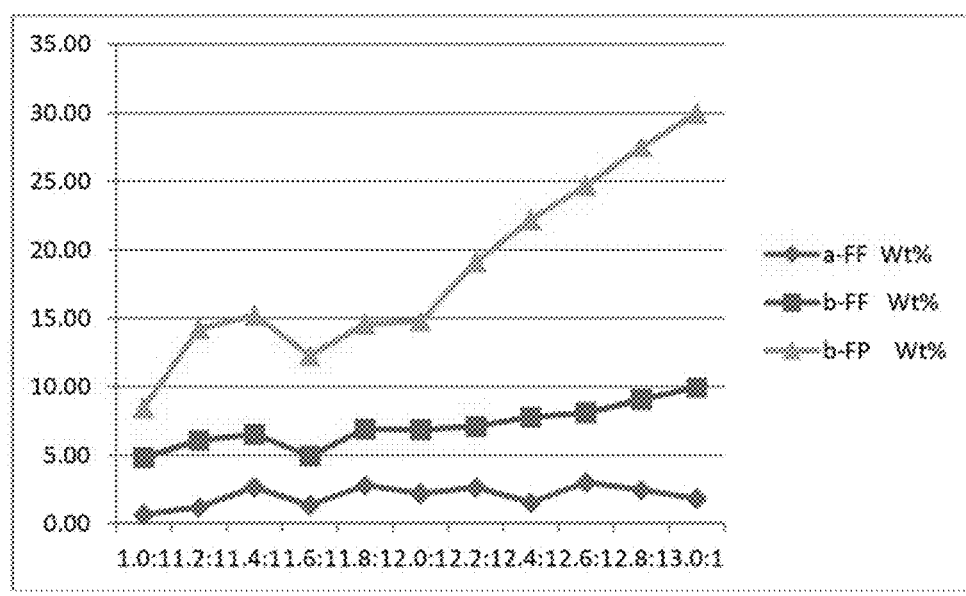

Likewise, $^{13}$C NMR analysis revealed that an increase in the molar ratio of carbohydrate (here:fructose) to boric acid increased unreacted carbohydrate (here:fructose) most significantly for the beta-fructopyranose form, moderately for the beta-fructofuranose form, and negligibly or not for the alpha-fructofuranose form as can be taken from Table 3 below. Once more, the most pronounced increase in unreacted carbohydrate for the beta-fructopyranose form and the beta-fructofuranose form started at a ratio of 1.6:1 or 1.8:1. Therefore, an increase of the molar ratio of carbohydrate (here:fructose) to boric acid above 1.6:1 or 1.8:1 had the unexpected technical effect of the unreacted carbohydrate for the beta-fructopyranose and the beta-fructofuranose forms as is also shown in FIG. 3D.

TABLE 3

| Molar Ratio | a-FF (wt %) | b-FF (wt %) | b-FP (wt %) |
|---|---|---|---|
| | Volume 200 ml | | |
| 1.0:1 | 0.66 | 4.84 | 8.49 |
| 1.2:1 | 1.19 | 6.09 | 14.24 |
| 1.4:1 | 2.65 | 6.55 | 15.21 |

TABLE 3-continued

| Molar Ratio | a-FF (wt %) | b-FF (wt %) | b-FP (wt %) |
|---|---|---|---|
| | Volume 200 ml | | |
| 1.6:1 | 1.35 | 4.96 | 12.26 |
| 1.8:1 | 2.80 | 6.95 | 14.57 |
| 2.0:1 | 2.20 | 6.88 | 14.79 |
| 2.2:1 | 2.65 | 7.14 | 19.14 |
| 2.4:1 | 1.54 | 7.80 | 22.19 |
| 2.6:1 | 3.02 | 8.11 | 24.67 |
| 2.8:1 | 2.46 | 9.07 | 27.53 |
| 3.0:1 | 1.83 | 9.93 | 30.00 |

Figure 3E:
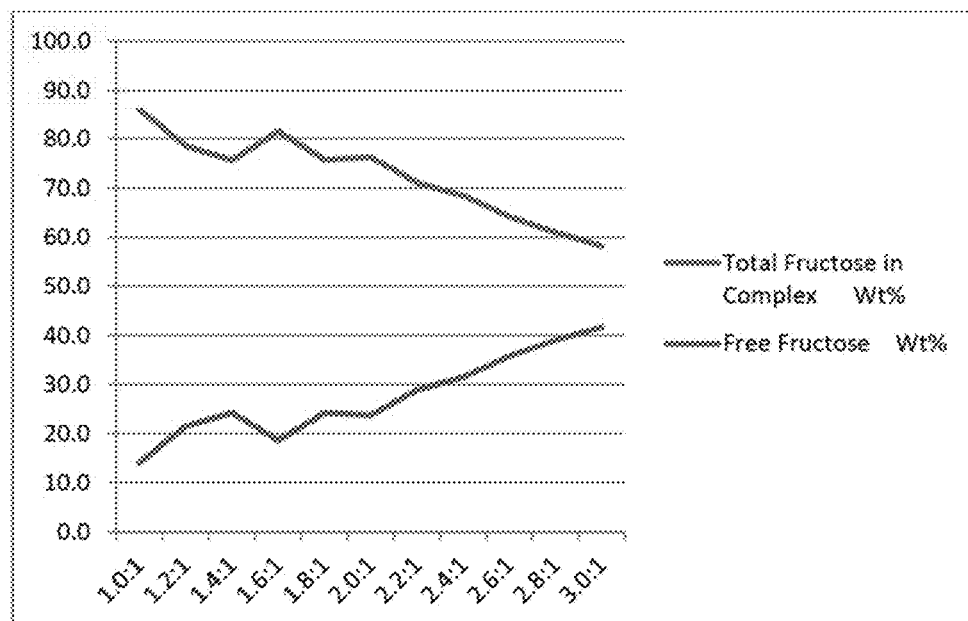
Figure 3F:
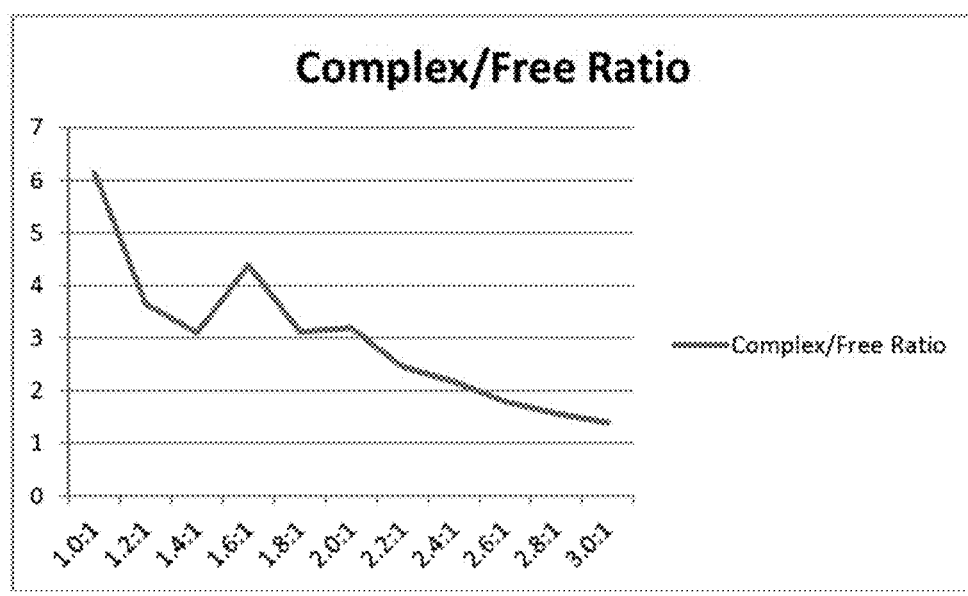

Tables 4 below demonstrates that the yield of fructose complexation is in inverse relation to increasing molar ratio of the carbohydrate to boric acid ratio. Notably, the yield of total fructose in complex as well as the specific yield (total fructose in complex relative to free total fructose) decreased with increasing molar ratio of the carbohydrate to boric acid ratio in counter trend to the yield for di-complex formation. Thus, it should be appreciated that various compositions with high specific di-complex yield at relatively high overall complex yields will typically be achieved where the reaction is performed at a molar ratio of the carbohydrate to boric acid of about 1.6:1 to 2.4:1. Selected results of Table 4 are exemplarily depicted in FIGS. 3E and 3F.

TABLE 4

| Molar Ratio | Total Fructose in Complex (wt %) | Free Fructose (wt %) | Complex:Free Ratio |
|---|---|---|---|
| | Volume 200 ml | | |
| 1.0:1 | 86.02 | 13.98 | 6.15 |
| 1.2:1 | 78.48 | 21.52 | 3.65 |
| 1.4:1 | 75.59 | 24.41 | 3.10 |
| 1.6:1 | 81.44 | 18.56 | 4.39 |
| 1.8:1 | 75.68 | 24.32 | 3.11 |
| 2.0:1 | 76.14 | 23.86 | 3.19 |
| 2.2:1 | 71.07 | 28.93 | 2.46 |
| 2.4:1 | 68.47 | 31.53 | 2.17 |
| 2.6:1 | 64.20 | 35.80 | 1.79 |
| 2.8:1 | 60.94 | 39.06 | 1.56 |
| 3.0:1 | 58.24 | 41.76 | 1.39 |

Figure 4A:
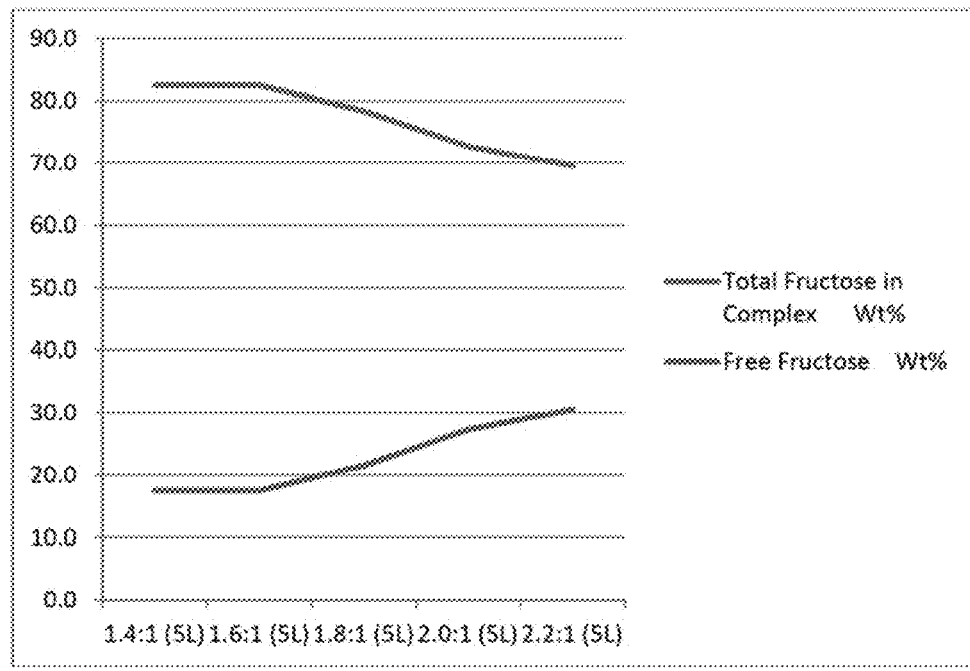
FIGS. 4A to 4B illustrate exemplary results for selected product parameters at a 5,000 ml scale and molar ratios of fructose to boric acid between 1.4:1 and 2.2:1.
Figure 4B:
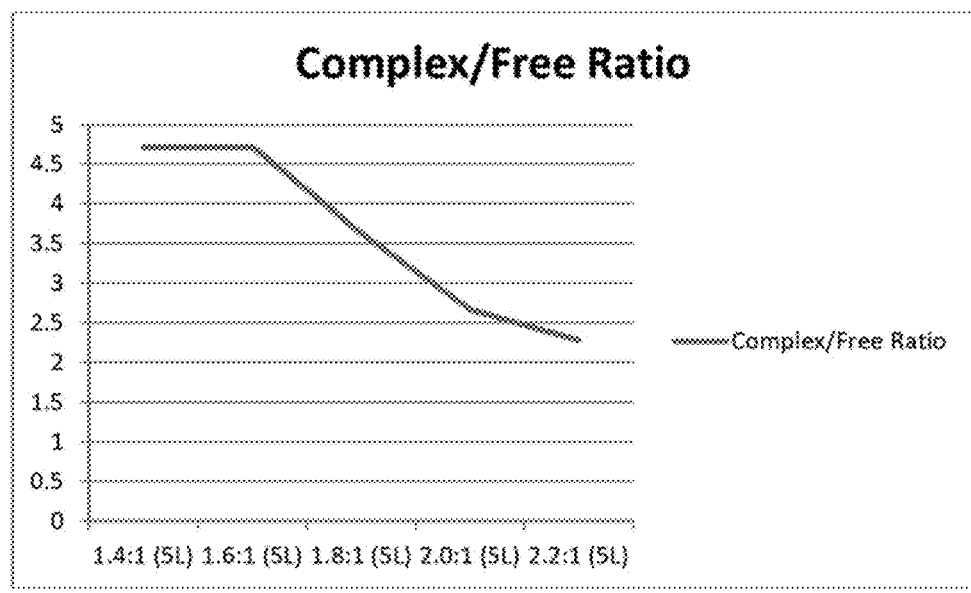

Such trend was also observed to be true where the production scale was increased from 200 ml to 1000 ml, to 5,000 ml, and even to 2,000 L as is shown in Table 5 below and selected results of Table 5 are shown in the graphs of FIGS. 4A and 4B.

TABLE 5

| Molar Ratio (scale) | α-FF-B-Complex Wt % | β-FF-B-Complex Wt % | β-FP-B-Complex Wt % | α-FF Wt % | β-FF Wt % | β-FP Wt % |
|---|---|---|---|---|---|---|
| 1:01 (1 L) | 50.6 | 18.4 | 17.0 | 0.7 | 4.8 | 8.5 |
| 1.2:1 (1 L) | 47.1 | 18.3 | 13.0 | 1.2 | 6.1 | 14.2 |
| 1.4:1 (1 L) | 46.4 | 17.7 | 11.5 | 2.6 | 6.5 | 15.2 |
| 1.6:1 (1 L) | 48.4 | 18.8 | 14.2 | 1.3 | 5.0 | 12.3 |
| 1.8:1 (1 L) | 45.0 | 17.8 | 12.9 | 2.8 | 6.9 | 14.6 |
| 2:01 (1 L) | 44.2 | 18.9 | 13.0 | 2.2 | 6.9 | 14.8 |
| 2.2:1 (1 L) | 43.0 | 18.1 | 10.0 | 2.6 | 7.1 | 19.1 |
| 2.4:1 (1 L) | 41.6 | 17.7 | 9.1 | 1.5 | 7.8 | 22.2 |
| 2.6:1 (1 L) | 39.0 | 17.9 | 7.3 | 3.0 | 8.1 | 24.7 |

TABLE 5-continued

| Molar Ratio (scale) | α-FF-B-Complex Wt % | β-FF-B-Complex Wt % | β-FP-B-Complex Wt % | α-FF Wt % | β-FF Wt % | β-FP Wt % |
|---|---|---|---|---|---|---|
| 2.8:1 (1 L) | 37.9 | 16.2 | 6.8 | 2.5 | 9.1 | 27.5 |
| 3:01 (1 L) | 36.0 | 16.5 | 5.7 | 1.8 | 9.9 | 30.0 |
| 1.4:1 (5 L) | 48.8 | 17.5 | 16.3 | 0.9 | 5.9 | 10.6 |
| 1.6:1 (5 L) | 46.5 | 19.2 | 16.3 | 0.9 | 5.9 | 10.6 |
| 1.8:1 (5 L) | 47.8 | 17.6 | 12.9 | 1.5 | 6.2 | 13.9 |
| 2:1 (5 L) | 44.6 | 18.3 | 9.8 | 1.4 | 7.2 | 18.6 |
| 2.2:1 (5 L) | 43.9 | 16.5 | 9.1 | 1.4 | 8.0 | 21.1 |
| 2.0:1 (2000 L) | | | | | | |

Table 6 further provides experimental data for the yield of total fructose in complex versus free fructose over a variety of molar ratios and production scales.

TABLE 6

| Molar Ratio (scale) | Total Fructose in Complex Wt % | Free Fructose Wt % |
|---|---|---|
| 1:01 (1 L) | 86.0 | 14.0 |
| 1.2:1 (1 L) | 78.5 | 21.5 |
| 1.4:1 (1 L) | 75.6 | 24.4 |
| 1.6:1 (1 L) | 81.4 | 18.6 |
| 1.8:1 (1 L) | 75.7 | 24.3 |
| 2:01 (1 L) | 76.1 | 23.9 |
| 2.2:1 (1 L) | 71.1 | 28.9 |
| 2.4:1 (1 L) | 68.5 | 31.5 |
| 2.6:1 (1 L) | 64.2 | 35.8 |
| 2.8:1 (1 L) | 60.9 | 39.1 |
| 3:01 (1 L) | 58.2 | 41.8 |
| 1.4:1 (5 L) | 82.5 | 17.5 |
| 1.6:1 (5 L) | 82.5 | 17.5 |
| 1.8:1 (5 L) | 78.4 | 21.6 |
| 2:1 (5 L) | 72.7 | 27.3 |
| 2.2:1 (5 L) | 69.5 | 30.5 |
| 2.0:1 (2000 L) | 77.8 | 22.2 |

Figure 5A:
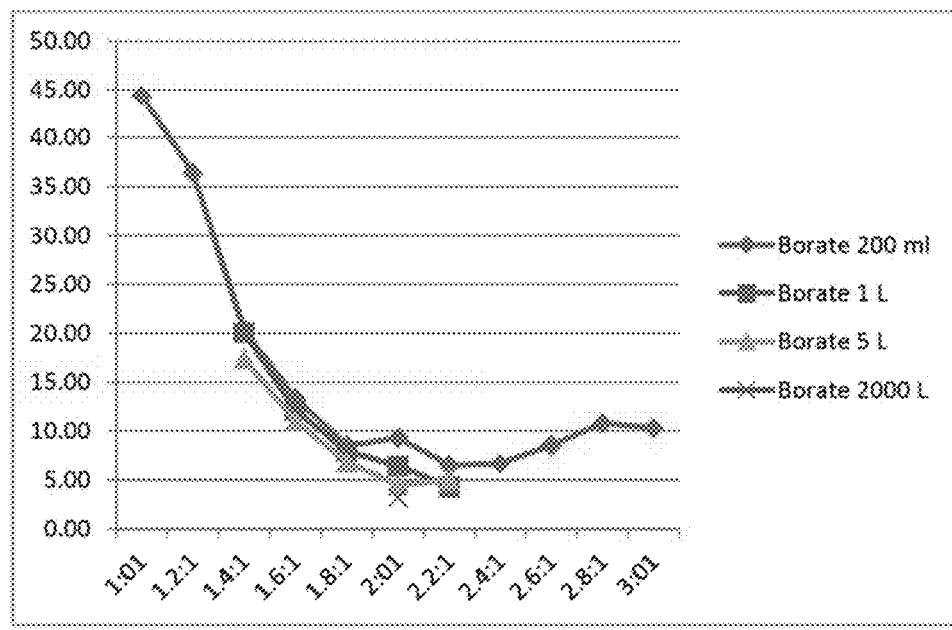
FIGS. 5A to 5E depict exemplary results for selected product parameters at escalating production scales and variable molar ratios of fructose to boric acid.
Figure 5B:
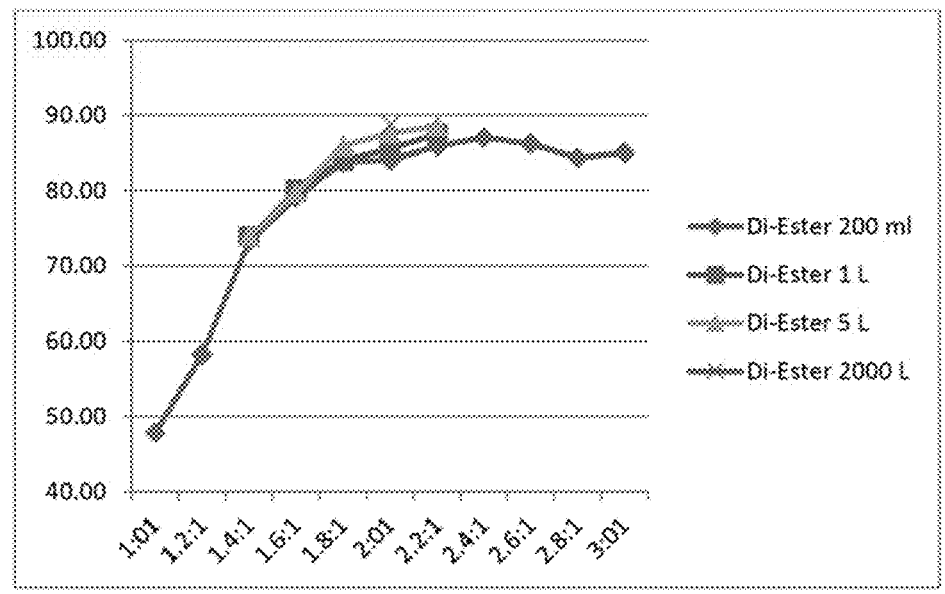
Figure 5C:
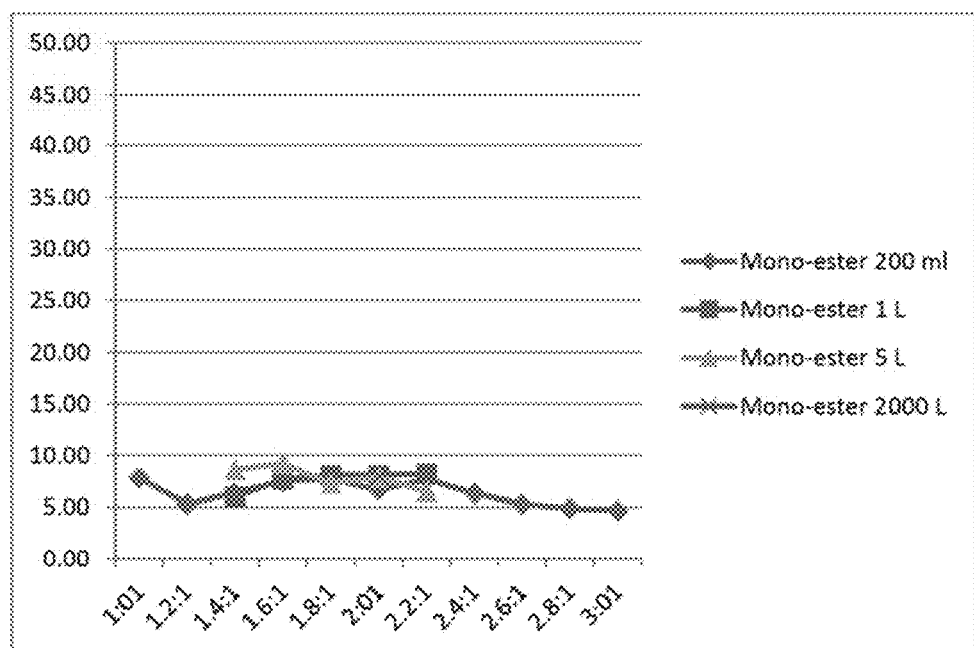

In yet another unexpected result during scale-up of the production volume, the inventors discovered that the production scale had substantial effect on both, the quantities of unreacted boric acid and the yield of di-ester formation for a given molar ratio. In short, and as can be taken from the data in Table 7, an increase in production scale at a given molar ratio of fructose to boric acid increased the yield of di-complex, while the same increase in production scale at a given molar ratio of fructose to boric acid decreased unreacted boric acid. Viewed from another perspective, and all other parameters being the same, the inventors discovered that an increase in production scale increased di-complex yield and decreased unreacted boric acid, while leaving the mono-ester substantially unaffected. FIG. 5A exemplarily shows this trend for unreacted boric acid, while FIG. 5B illustrates the trend for di-ester formation, and FIG. 5C shows results for the mono-ester yields. Thus, it should be appreciated that scale-up (with all other parameters being identical) had a rather unexpected technical effect of increasing the yield of di-complex, and decreasing quantities of unreacted boric acid.

TABLE 7

| Molar Ratio | Borate | | | | Di-Ester | | | | Mono-ester | | | |
|---|---|---|---|---|---|---|---|---|---|---|---|---|
| | 200 ml | 1 L | 5 L | 2000 L | 200 ml | 1 L | 5 L | 2000 L | 200 ml | 1 L | 5 L | 2000 L |
| 1.0:1 | 44.34 | | | | 47.84 | | | | 7.82 | | | |
| 1.2:1 | 36.42 | | | | 58.26 | | | | 5.32 | | | |
| 1.4:1 | 20.32 | 20.10 | 17.40 | | 73.28 | 73.90 | 74.00 | | 6.40 | 6.00 | 8.60 | |
| 1.6:1 | 13.38 | 12.10 | 11.00 | | 79.12 | 80.20 | 79.80 | | 7.50 | 7.70 | 9.20 | |
| 1.8:1 | 8.46 | 7.90 | 6.80 | | 83.84 | 84.00 | 85.90 | | 7.70 | 8.10 | 7.30 | |
| 2.0:1 | 9.28 | 6.40 | 4.50 | 3.20 | 84.04 | 85.50 | 87.60 | 88.80 | 6.68 | 8.10 | 7.90 | 8.00 |
| 2.2:1 | 6.46 | 4.30 | 5.00 | | 85.86 | 87.50 | 88.50 | | 7.67 | 8.20 | 6.50 | |
| 2.4:1 | 6.64 | | | | 87.01 | | | | 6.35 | | | |
| 2.6:1 | 8.50 | | | | 86.19 | | | | 5.31 | | | |
| 2.8:1 | 10.78 | | | | 84.33 | | | | 4.89 | | | |
| 3.0:1 | 10.31 | | | | 85.02 | | | | 4.68 | | | |

Figure 5D:
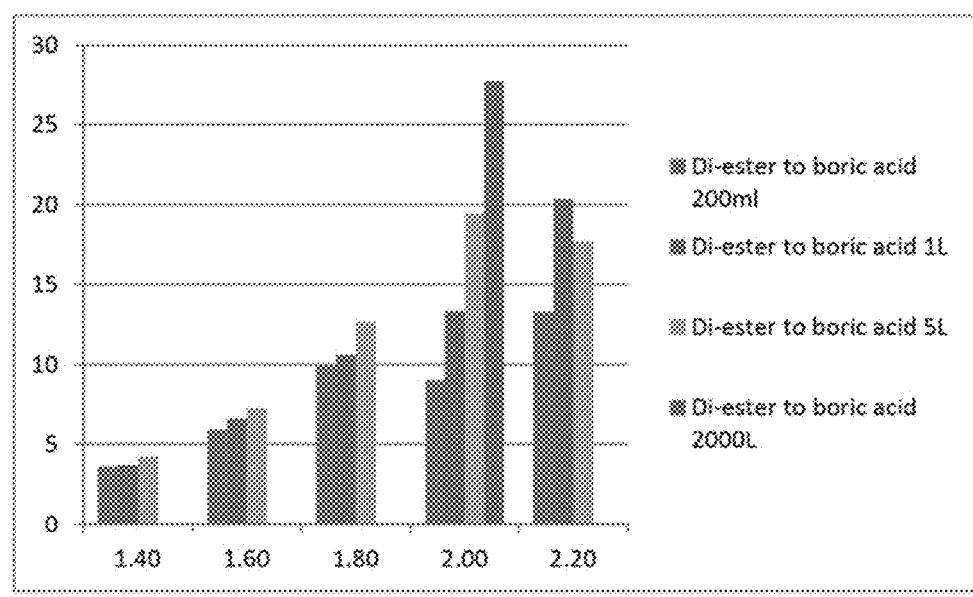

Remarkably, as can be readily appreciated from FIG. 5D, the scale-dependent increase of the di-ester to boric acid ratio was particularly pronounced for a specific range of molar ratios, while being less pronounced for other molar ratios. More specifically, scale-dependent increase of the di-ester to boric acid ratio was especially evident for the range of molar ratios between 1.8:1 and 2.2:1 as is also reflected in Table 8 below.

discovered that drying (e.g., via freeze-drying "FD" and spray-drying "SD") further dramatically increased di-complex to boric acid ratios in a substantially independent manner of the kind of water removal. Selected exemplary data are provided in Table 11 below using a single molar ratio of 2:1 (fructose to boric acid) at the listed production scales. Reconstitution was performed with $D_2O$ to original volume prior to water removal (i.e., at a dry ratio of between about 2.2 to 3.5 by weight).

TABLE 11

| | 2:1 Molar Ratio Only | | | | | | | | |
|---|---|---|---|---|---|---|---|---|---|
| | 200 ml | | | 1 liter | | | 5 liters | | |
| | Liquid | FD | SD | Liquid | FD | SD | Liquid | FD | SD |
| dry ratio | N/A | 2.42 | 2.7 | N/A | 3.2 | 3.5 | N/A | 2.6 | 3.3 |
| Borate | 9.28 | 5 | 4.7 | 6.4 | 4.3 | 4.1 | 4.5 | 3.7 | 3.9 |
| Di-complex | 84.04 | 86.9 | 86.9 | 85.5 | 86.2 | 87.9 | 87.6 | 86.5 | 87.1 |
| mono-complex | 6.68 | 8.1 | 8.4 | 8.1 | 8.5 | 8.6 | 7.9 | 9.9 | 9.3 |

TABLE 8

| Molar | Di-ester to Borate Ratio | | | |
|---|---|---|---|---|
| Ratio | 200 ml | 1 L | 5 L | 2000 L |
| 1.4 | 3.61 | 3.68 | 4.25 | |
| 1.6 | 5.91 | 6.63 | 7.25 | |
| 1.8 | 9.91 | 10.63 | 12.63 | |
| 2.0 | 9.05 | 13.36 | 19.47 | 27.75 |
| 2.2 | 13.28 | 20.35 | 17.70 | |

Figure 5E:
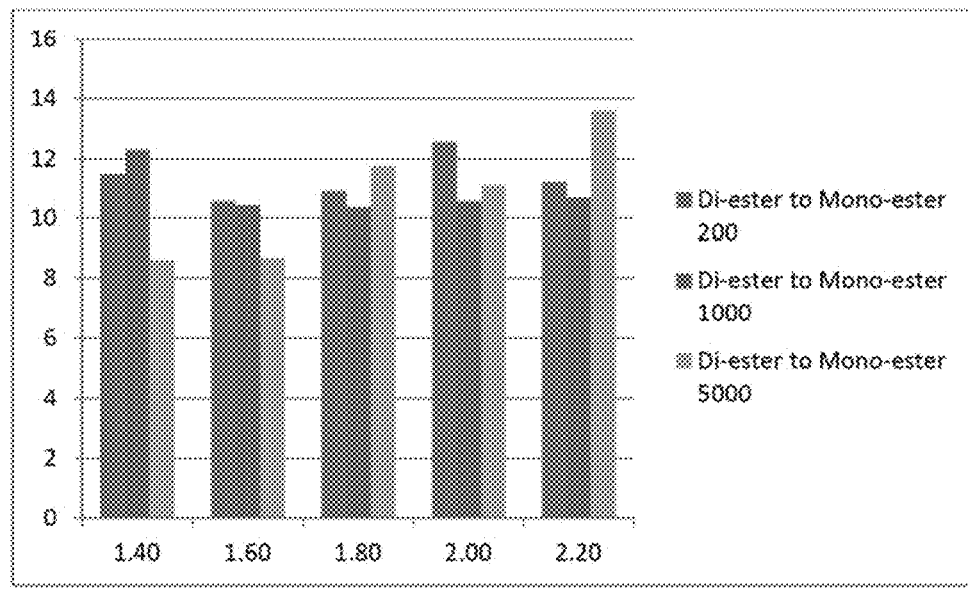

Notably, the di-ester to mono-ester ratio was substantially unaffected by the increase in production scale as is reflected in FIG. 5E and the results of Table 9 below.

TABLE 9

| Molar | Di-ester to Mono-ester Ratio | | |
|---|---|---|---|
| Ratio | 200 | 1000 | 5000 |
| 1.4 | 11.45 | 12.32 | 8.60 |
| 1.6 | 10.55 | 10.42 | 8.67 |
| 1.8 | 10.89 | 10.37 | 11.77 |
| 2.0 | 12.58 | 10.55 | 11.09 |
| 2.2 | 11.19 | 10.67 | 13.61 |

Exemplary pH values for various production scales shows the acidity to be substantially uniform in the (mildly) acidic range, generally below 7, in many cases below 6.5, and in most cases at or below 6 as can be seen from Table 10 below.

TABLE 10

| Molar Ratio | 1 L pH | 5 L pH | 2000 L pH |
|---|---|---|---|
| 1.4:1 | 5.72 | 5.23 | |
| 1.6:1 | 5.73 | 5.64 | |
| 1.8:1 | 5.69 | 5.64 | |
| 2.0:1 | 5.64 | 5.57 | 5.96 |
| 2.2:1 | 5.64 | 5.51 | |

Figure 6A:
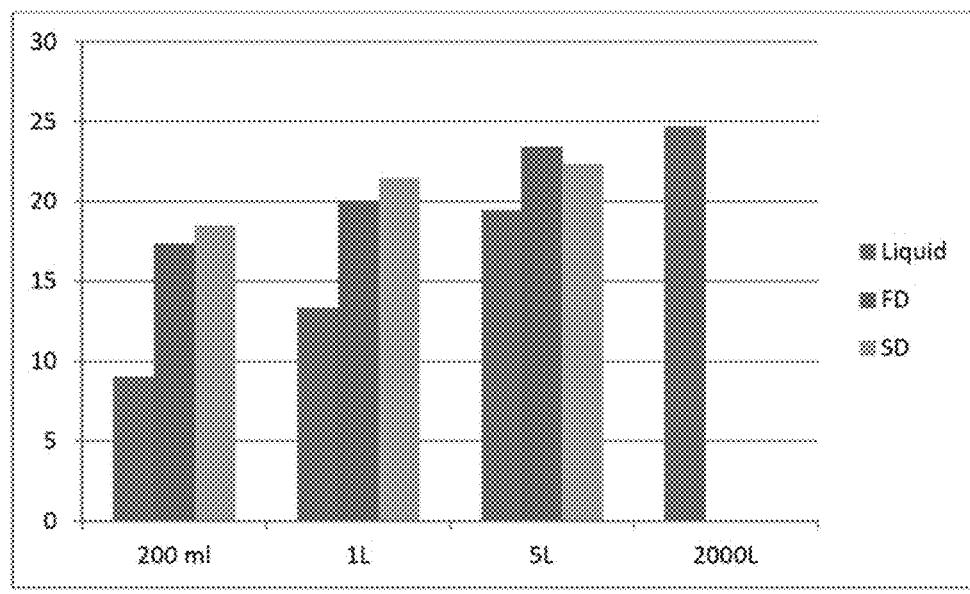
FIGS. 6A to 6B show exemplary results for selected product parameters of reconstituted compositions after water had been removed using a fixed molar ratio between fructose and boric acid.
Figure 6B:
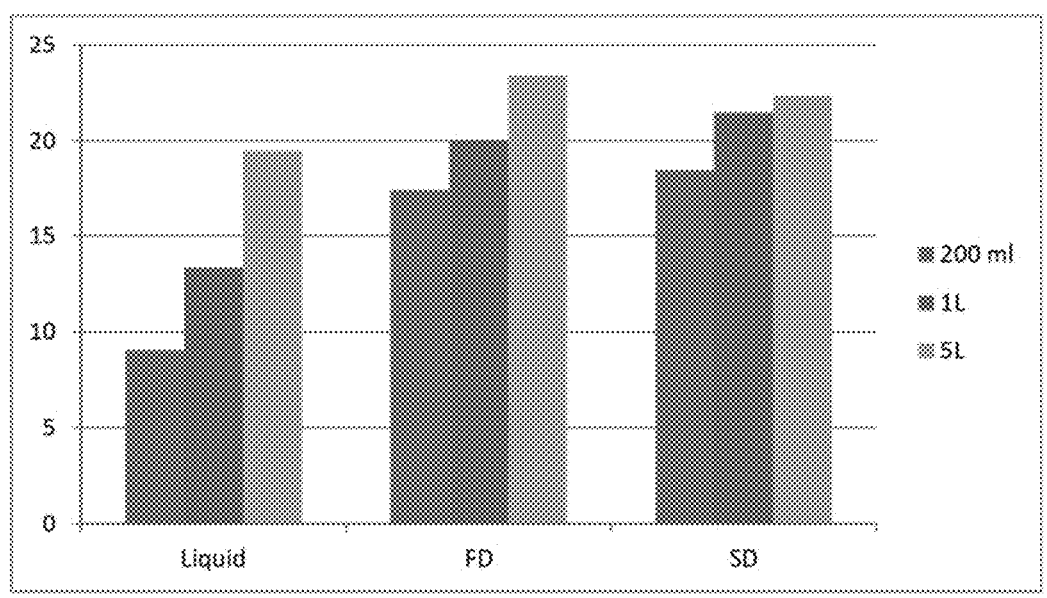

The inventors further investigated whether or not at least water removal from the finished reaction would further affect the product composition. Surprisingly, the inventors FIG. 6A illustrates the change in di-complex to boric acid ratio as a function of drying method for each of the production volumes, while Table 12 below and FIG. 6B show the change in di-complex to boric acid ratio as a function of production volumes for each of the drying methods.

TABLE 12

| Ratio Di-complex to Borate | | | | | | | | |
|---|---|---|---|---|---|---|---|---|
| 200 ml | | | 1 liter | | | 5 liters | | |
| Liquid | FD | SD | Liquid | FD | SD | Liquid | FD | SD |
| 9.06 | 17.38 | 18.49 | 13.36 | 20.05 | 21.44 | 19.47 | 23.38 | 22.33 |

Thus, it should be noted that removal of water, and especially drying of the liquid compositions has the unexpected technical effect of substantially increasing the di-complex to unreacted boric acid ratio, with a substantial increase of di-complex and a concomitant decrease in unreacted boric acid.

In some embodiments, the numbers expressing quantities of ingredients, properties such as concentration, reaction conditions, and so forth, used to describe and claim certain embodiments of the invention are to be understood as being modified in some instances by the term "about." Accordingly, in some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the invention are approximations, the numerical values set forth in the specific examples are reported as precisely as practicable. The numerical values presented in some embodiments of the invention may contain certain errors necessarily resulting from the standard deviation found in their respective testing measurements. Unless the context dictates the contrary, all ranges set forth herein should be interpreted as being inclusive of their endpoints and open-ended ranges should be interpreted to include only commercially practical values.

Similarly, all lists of values should be considered as inclusive of intermediate values unless the context indicates the contrary.

The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the invention and does not pose a limitation on the scope of the invention otherwise claimed. No language in the specification should be construed as indicating any non-claimed element essential to the practice of the invention.

It should be apparent to those skilled in the art that many more modifications besides those already described are possible without departing from the inventive concepts herein. The inventive subject matter, therefore, is not to be restricted except in the spirit of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification claims refers to at least one of something selected from the group consisting of A, B, C . . . and N, the text should be interpreted as requiring only one element from the group, not A plus N, or B plus N, etc.

What is claimed is:

1. A method of producing a boron-containing composition with a borocarbohydrate di-complex content of at least 85 wt % and residual boric acid of no more than 7 wt %, comprising:
   reacting at a scale of at least 5,000 ml boric acid with an oligosaccharide and/or a polysaccharide to form a plurality of borocarbohydrate complexes and residual boric acid;
   wherein the molar ratio between the oligosaccharide and/or the polysaccharide to boric acid is about 2.0:1;
   wherein the step of reacting is performed in an aqueous solution having a pH of less than 6.0.

2. The method of claim 1 wherein the oligosaccharide is a disaccharide.

3. The method of claim 2 wherein the disaccharide comprises at least one of fructose, glucose, arabinose, and galactose.

4. The method of claim 1 wherein the polysaccharide is a nutritionally acceptable polysaccharide.

5. The method of claim 4 wherein the polysaccharide is a starch or a pectin.

6. The method of claim 1 wherein the residual boric acid is present in the composition after the step of reacting in an amount of less than 8.0 wt %.

7. The method of claim 1 wherein the residual boric acid is present in the composition after the step of reacting in an amount of less than 5.0 wt %.

8. The method of claim 1 further comprising, after the step of reacting, a step of charge neutralizing the borocarbohydrate complexes with a cation-containing compound.

9. The method of claim 8 wherein the cation-containing compound is an alkaline metal hydroxide, an earth alkaline metal hydroxide, an alkaline metal carbonate, and/or an earth alkaline metal carbonate.

10. The method of claim 1 wherein the pH is between 5.0 and 6.0.

11. The method of claim 1 further comprising a step of removing the aqueous solution.

12. The method of claim 11 wherein the step of removing the aqueous solution is spray drying or freeze-drying.

13. The method of claim 1 further comprising a step of including the boron-containing composition or the borocarbohydrate complexes into a nutritionally acceptable carrier.

14. The method of claim 13 wherein the nutritionally acceptable carrier is a beverage.

15. The method of claim 14 wherein the boron-containing composition or the borocarbohydrate complexes are formulated into a nutritional supplement.

16. The method of claim 1 wherein the nutritionally acceptable carrier is a solid carrier.

17. The method of claim 1 further comprising a step of combining the boron-containing composition or the borocarbohydrate complexes with another nutritionally acceptable ingredient.

18. The method of claim 1 wherein the borocarbohydrate complexes have an association constant of at least 250.

* * * * *